United States Patent [19]

Kohigashi et al.

[11] Patent Number: 4,921,351
[45] Date of Patent: May 1, 1990

[54] SPECTROPHOTOMETER COMPRISING A XENON FLASHTUBE AS A LIGHT SOURCE

[75] Inventors: Taiji Kohigashi, Suita; Miki Koyama, Sakai, both of Japan

[73] Assignee: Kurashiki Boseki Kabushiki Kaisha, Okayama, Japan

[21] Appl. No.: 240,617

[22] Filed: Sep. 6, 1988

[30] Foreign Application Priority Data

Sep. 4, 1987 [JP] Japan ................................ 62-222454

[51] Int. Cl.⁵ .......................... G01J 3/42; G01N 21/55
[52] U.S. Cl. .................................... 356/323; 250/228; 356/236; 356/448
[58] Field of Search ........................ 356/323, 236, 448; 250/228

[56] References Cited

U.S. PATENT DOCUMENTS 3,458,261  7/1969  Bentley et al. ................... 250/228 X
4,687,329  8/1987  Schultz .............................. 356/328
4,753,530  6/1988  Knight et al. ..................... 356/448 X

FOREIGN PATENT DOCUMENTS 56-122936  9/1981  Japan ................................ 356/448

OTHER PUBLICATIONS

Kishner, "A Pulsed-Xenon Spectrophotometer with Parallel Wavelength Sensing", Proceedings of the Third Congress of the International Color Association, Troy, N.Y., USA, 10-15 Jul. 1977, pp. 305-308.

Primary Examiner—Vincent P. McGraw
Attorney, Agent, or Firm—Wenderoth, Lind & Ponack

[57] ABSTRACT

The present invention is drawn to a spectrophotometer using a pulsed xenon flashtube as a light source. The energy to be applied to the light source of the spectrophotometer is set within a range of 0.03 joules to 1.0 joule. Therefore, the intensity of light emitted from the light source is not too great, which allows the spectrophotometer to measure a spectral reflectance under the presence of natural light or equivalents thereof. Further, the charging period of time required for the spectrophotometer to provide a desired light emission intensity is short, so that the light source is capable of emitting many flashes of light per second, wherein the amount of data produced within a predetermined measuring period is increased. Thus, accurate data can be generated.

6 Claims, 3 Drawing Sheets

SPECTROPHOTOMETER COMPRISING A XENON FLASHTUBE AS A LIGHT SOURCE

BACKGROUND OF THE INVENTION

1. Field of the Invention

The present invention relates to a spectrophotometer, and more particularly, to a spectrophotometer using a pulsed xenon flashtube.

2. Description of Related Art

A spectrophotometer is used to make measurements of the spectral reflectance of an object within a predetermined period of time and to perform a color matching operation. While the optical configuration of the spectrophotometer is capable of taking many forms, the like source thereof irradiates a sample and the light reflected from the sample is introduced into a spectroscope so that spectrum reflectance data can be obtained.

While the spectrophotometer uses various light sources therein, it normally uses a tungsten lamp. In order for the tungsten lamp to provide reliable spectrum reflectance data, it is necessary that the signal-to-noise ratio ((S/N) ratio) thereof be high which is effected by the emission of an intense light from the light source thereof. However, the tungsten lamp has a disadvantage in that the heat givent off thereby is great when the light emission intensity is high.

U.S. Pat. No. 4,076,421 or its corresponding Japanese Patent Publication No. 52183/1978 discloses a spectrophotometer using a pulsed xenon flashtube as the light source thereof. The xenon flashtube emits a small amount of heat and has a high S/N ratio compared with a tungsten tube. The reason why the pulsed xenon flashtube is used as the light source is because the spectral content thereof is extremely stable and enables a compensation for flash-to-flash variations using a single broadband-response photodetector. That is, the high intensity and short- pulse width renders an electronic circuit which is high-pass filtered extremely insensitive to the effects of ambient light. Thus, the known spectrophotometer is intended to allow the light source thereof to emit an intense light. It is to be noted herein that 15 joules of energy is applied to spectrophotometers according to U.S. Pat. No. 4,076,421 and that the xenon flashtube provides a short intense pulse of illumination of approximately tens of microseconds duration.

However, when a spectral reflectance is determined using a light source which provides such an intense pulse of illumination by applying a great amount of energy to a spectrophotometer, the following occurs. Light may permeate deep into the sample to a great extent depending on the surface structure of the sample. Thus, even undesired information of the sample may be obtained. Data obtained using such a spectrophotometer has no correlation to the data obtained under natural light (or equivalents thereof). The intensity of light emitted from the light source of the spectrophotometer fluctuates to a great extent. Therefore, when the spectral reflectance of the sample having a high reflection factor is detected, it is difficult to compensate for the fluctuation of the intensity of the light reflected therefrom. Thus, accurate data of the spectral reflectance cannot be obtained.

In addition, the period of time required for charging the spectrophotometer, namely, the flash-to-flash period takes as long as one second in order to provide a short, intense pulse of illumination of tens of microseconds by inputting 15 joules of energy to the spectrophotometer. Accordingly, the spectrophotometer flashes only approximately four to ten times within a predetermined period of time during a spectral reflectance-measuring operation.

SUMMARY OF THE INVENTION

The present invention has been developed to solve the above-described problems and has as its essential object to provide a spectrophotometer which is capable of measuring the spectral reflectance of an object using a pulsed xenon flashtube under a natural light (or equivalents) and emits flashes of light many times within a predetermined measuring time, thus providing highly accurate data.

In accomplishing this and other objects, in a spectrophotometer according to one preferred embodiment of the present invention, the energy to be applied to the spectrophotometer comprising a pulsed xenon flashtube is set to be within a range of 0.03 joules to 1.0 joule.

According to the spectrophotometer in accordance with the present invention, the spectral content of light emitted from the pulsed xenon flashtube is very reliable and the S/N ratio thereof is high, and further, the use of a single broadband-response photodetector enables the compensation for emission-to-emission intensity variations of the light source of the spectrophotometer. In addition, since the energy applied to the spectrophotometer is set to be 0.03 joules or more and 1.0 joule or less, a spectral reflectance of the object can be measured under natural light (or equivalents thereof). Furthermore, the period of time required for the light source to be charged is short before the light source emits a light having a desired intensity. Accordingly, the light source emits flashes of light as many as 10 to 36 times per second. In other words, the spectrophotometer provides more data within a predetermined period of time, which leads to the generation of accurate data.

When the energy to be applied to the spectrophotometer is below 0.03 joules, the intensity of the light emitted from the light source is weak, and the S/N ratio thereof is low. In this case, the accuracy of measurements of the spectral reflectance is poor. On the other hand, when the energy to be applied thereto is above 1.0 joule, the intensity of the light emitted from the light source is too intense, so that the condition in which the spectral reflectance is measured differs greatly from the condition in which natural light or equivalents thereof are present.

As apparent from the foregoing description, the following advantages can be obtained according to the present invention.

The spectral reflectance of a sample can be measured using the pulsed xenon flashtube under a condition in which natural light or equivalents thereof are present. Further, the light source emits flashes of light many times within a predetermined measuring period, thereby facilitating the generation of accurate data.

BRIEF DESCRIPTION OF THE DRAWINGS

These and other objects and feature of the present invention will become apparent from the following description taken in conjunction with the preferred embodiment thereof with reference to the accompanying drawings, in which.

DETAILED DESCRIPTION OF THE PREFERRED EMBODIMENTS

One preferred embodiment of the present invention is described hereinbelow with reference to FIGS. 1 through 3.

Figure 1:
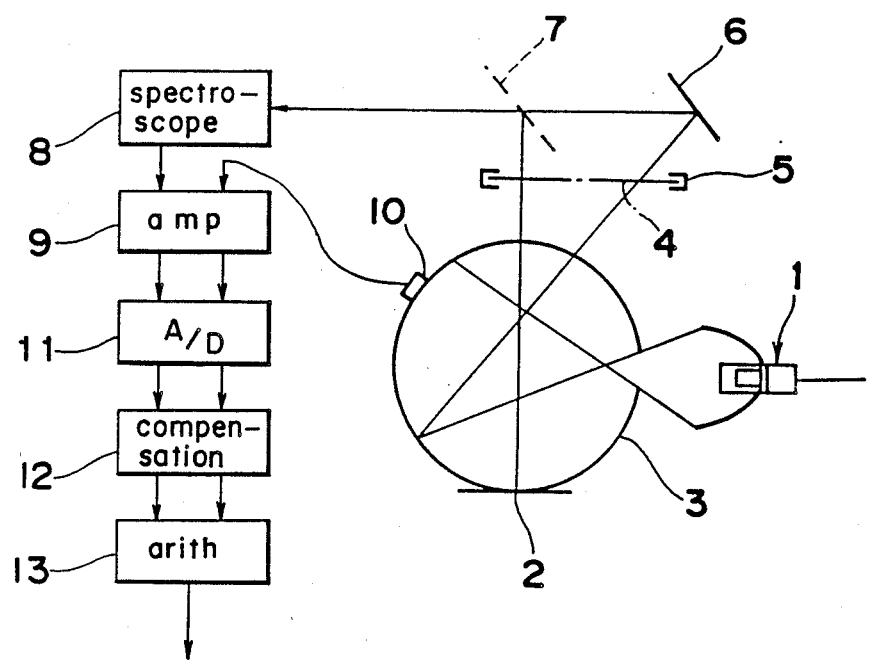
FIG. 1 is a schematic diagram of a spectrophotometer according to one embodiment of the present invention.

FIG. 1 is a schematic diagram of a spectrophotometer according to one preferred embodiment of the present invention. A pulsed xenon flashtube is used as a light source 1. The energy to be applied to the spectrophotometer can be set within a range of 0.03 to 1.0 joule. A sample 2 is placed at a lower aperture of an integrating sphere 3. A rotary chopper 4 is disposed above the integrating sphere 3. The rotation of the rotary chopper 4 at a constant speed allows the alternate introduction of light reflected from a sample (hereinafter referred to as sample light) and light reflected from the inner circumferential see face of the integrating sphere 3 (hereinafter referred to as reference light) into a spectroscope 8 having photodetectors. A switching means having the same function as the rotary chopper 4, namely, the function of alternately allowing the sample light and the reference light to be introduced into the spectroscope 8 may be provided instead of the rotary chopper 4. A photosensor is provided on the outer periphery of the rotary chopper 4 to serve as a synchronizing sensor 5. The synchronizing sensor 5 allows the light source 1 to emit light according to the rotational speed of the rotary chopper 4. The synchronizing sensor 5 detects that the rotary chopper 4 is at the position at which the rotary chopper 4 allows the sample light or the reference light to be introduced into the spectroscope 8, thus outputting to the light source 1 a trigger signal for causing the light emission from the light source 1. In addition, the synchronizing sensor 5 outputs to a reflectance factor arithmetic circuit 13 a distinguishing signal for distinguishing the kind of data transmitted from the integrating sphere 3 thereto. The spectrophotometer further comprises a mirror 6 for reflecting the reference light and introducing it into the spectroscope 8, and a half mirror 7 for introducing the sample light into the spectroscope 8. A light source intensity-sensor 10 is disposed in a window of the integrating sphere 3 a certain distance from the location at which the sample 2 is disposed. The light source-intensity sensor 10 detects the intensity of light every time the light source 1 emits a flash of light. The fluctuation of the intensity of the light emitted from the light source 1 can be compensated for by finding the ratio of data values (the intensities of the sample light and the reference light) to the intensity of the light reflected from the light source 1. That is, the fluctuation of the intensity of the light source 1 can be compensated for by finding the ratio of the intensity of the sample light to the intensity of the light emitted from the light source 1 and the ratio of the intensity of the reference light to the intensity of the light emitted from the light source 1.

Separate spectroscopes 8 may be provided in positions at which they are, respectively, capable of receiving the sample light and the reference light so that signals can be transmitted therefrom to an amplifier 9. Thus, the means having the function of allowing the sample light and the reference light to be introduced into the spectroscope 8 and the synchronizing sensor 5 can be omitted from the spectrophotometer.

The signals corresponding to the spectral data outputted from the spectroscope 8 and the signals corresponding to the the intensity of the light emitted from the light source 1 obtained by the light source intensity-sensor 10 are inputted to a compensation circuit 12, and thereafter, to the reflectance factor arithmetic circuit 13 through the amplifier 9 and an analog-to-digital converter 11. The compensation circuit 12 calculates the ratio (A) of the the intensity of the sample light to the intensity of the light emitted from the light source 1 and the ratio (B) of the intensity of the reference light to the intensity of the light emitted from the light source 1. The reflectance factor arithmetic circuit 13 calculates the ratio (A) to the ratio (B). The reflectance factor arithmetic circuit 13 outputs the ratio A/B as the spectral reflectance of the sample 2. In addition, the circuits 12 and 13 can be replaced by a microcomputer which perform the same functions as those of the circuits 12 and 13.

Figure 2:
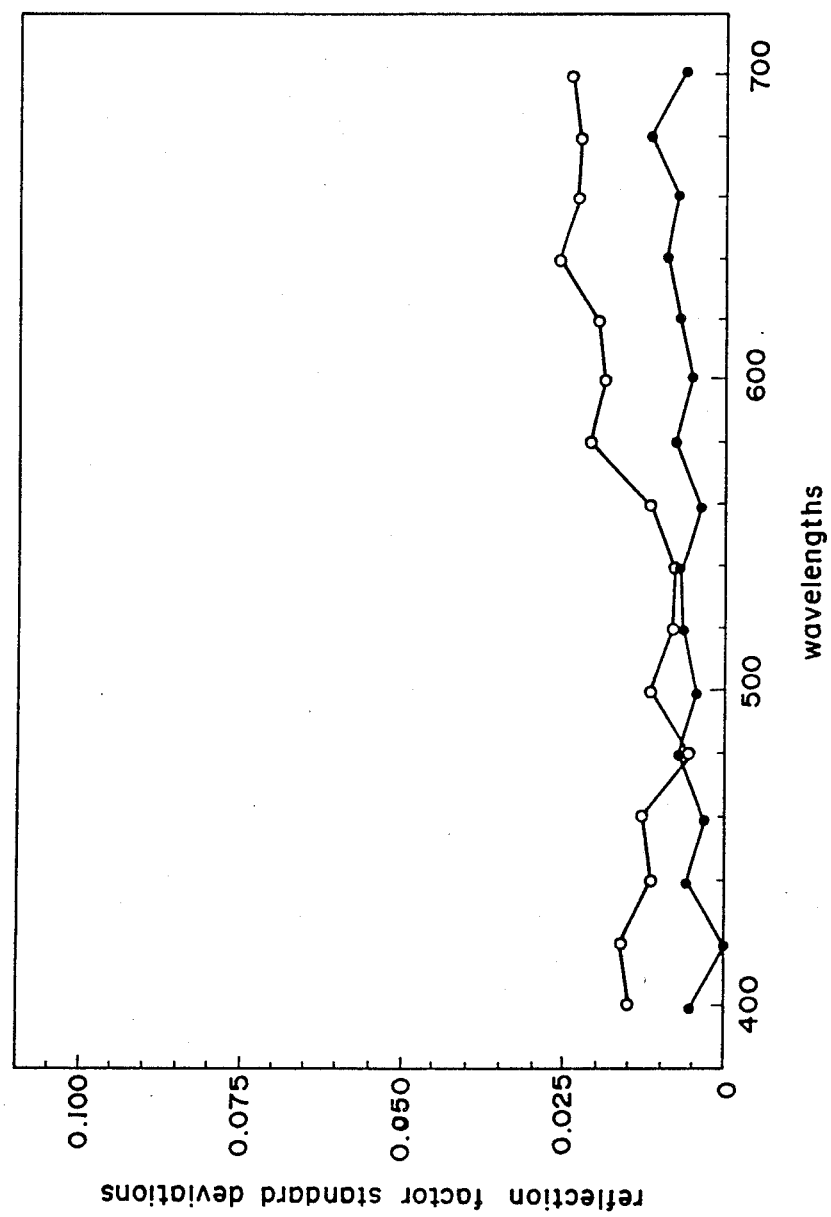
FIG. 2 is a graph showing the results obtained in a test conducted to measure the reproducibility of the spectral reflectance of respective wavelengths according to an embodiment of a spectrophotometer of the present invention.
Figure 3:
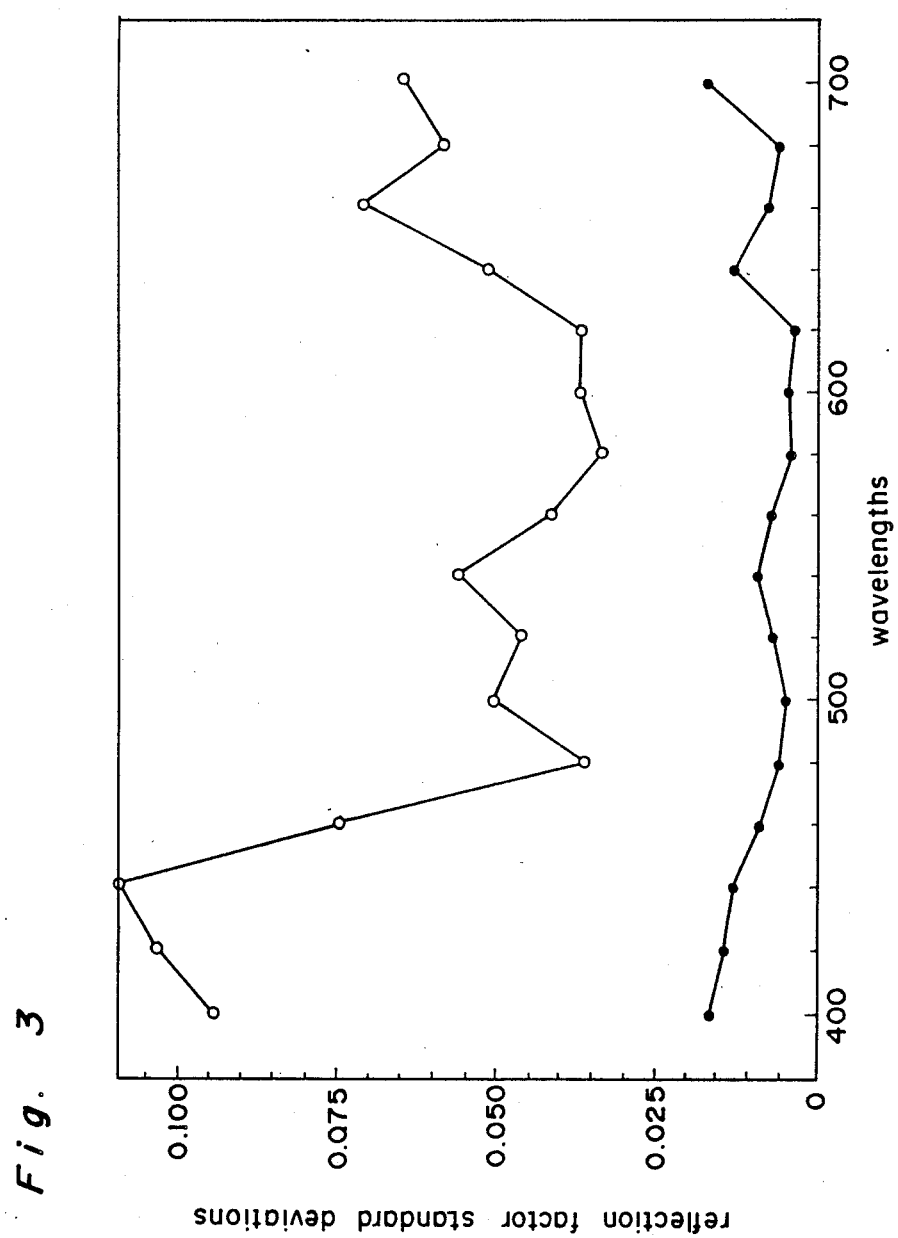
FIG. 3 is a graph showing the results obtained in a test conducted to measure the reproducibility of the spectral reflectance of respective wavelengths on the same sample and in a similar condition according to a known spectrophotometer.

FIG. 2 is a graph showing the result obtained from tests conducted by a spectrophotometer according to the present invention of the reproducibilities of the spectral reflectances of respective wavelengths. FIG. 3 is a graph showing the results obtained from tests conducted by a known spectrophotometer on the same sample and in the same condition. The ordinates shown in FIGS. 2 and 3 indicate reflection factor standard deviations, and the abscissas shown in FIGS. 2 and 3 indicate wavelengths. In the tests, ceramic white plates are used as samples having high reflection factors and black velvet samples are used as samples having low reflection factors. The polygonal lines formed by plotting measuring points "o" show data obtained from the samples having the high reflection factors, and those formed by plotting measuring points "●" show data obtained from the samples having the low reflection factors. In the tests using the spectrophotometer according to the present invention, 0.15 joules of energy was applied to the light source 1. The known spectrophotometer emits a flash of light once a second whereas the spectrophotometer according to the present invention emits flashes of light 16 times per second. As the graphs show, according to the tests using the conventional spectrophotometer, the spectral reflectance of the sample having the high spectral reflectance greatly fluctuates whereas according to the embodiment of the present invention, the fluctuation of the spectral reflectance of the sample having the high spectral reflectance is very small. Even the fluctuation of the spectral reflectance of the sample having the low spectral reflectance obtained using the spectrophotometer according to the present invention is equal to or smaller than that of the spectral reflectance obtained using the known spectrophotometer.

In this embodiment, the fluctuation of the intensity of light emitted from the light source 1 is compensated for by the ratio of the data values (light emission intensities of the sample light and the reference light) to the intensity of the light emitted from the light source 1 every time the light source 1 emits a flash of light; however, the compensation can be made as well by finding the ratio of the sum of the emission light intensities of the sample light to the sum of the intensities of the flashes of light emitted from the light source 1, and the ratio of the sum of the light emission intensities of the reference light to the sum of the light intensities of the flashes of light emitted from the light source 1. According to this method, the period of time required for performing an arithmetic calculation is shortened for compensating for the fluctuation of the intensity of flashes of light emitted from the light source 1, and further, the accuracy of the spectral reflectance obtained by this method is almost equal to that of the embodiment described above.

In addition to the above-described embodiment, it is preferable to further improve the measuring accuracy of the spectrophotometer according to the present invention by providing the spectrophotometer with means for detecting the fluctuation of the intensity of the flashes of light emitted from the light source 1 according to a signal inputted thereto and performing a feedback control in response to the signal so that the energy to be applied to the spectrophotometer is controlled, thus reducing the fluctuation in the intensity of the light emitted from the light source 1.

What is claimed is:

1. A spectrophotometer comprising a pulsatable xenon flashtube for emitting flashes of light when energy is input thereto, energy input means operatively connected to said xenon flashtube for inputting 0.03 to 1.0 joules of energy to said xenon flashtube, and detecting means for detecting the intensity of respective wavelengths of light which has been emitted from said xenon flashtube.

2. A spectrophotometer as claimed in claim 1, wherein said pulsatable xenon flashtube emits 10 to 36 flashes of light per second.

3. A spectrophotometer as claimed in claim 1, and further comprising an integrating sphere including a light-reflecting inner surface and means for exposing a sample at the inner surface, said integrating sphere being disposed in the spectrophotometer so as to receive therein flashes of light emitted by said pulsatable xenon flashtube;
   a light sensor for sensing the intensity of the flashes of light as emitted by said xenon flashtube;
   and wherein said detecting means includes at least one spectroscope for detecting the intensity of respective wavelengths of light reflected from the inner surface of said integrating sphere and for detecting the intensity of respective wavelengths of light reflected from a sample exposed at the inner surface of said integrating sphere.

4. A spectrophotometer as claimed in claim 1, and further comprising an integrating sphere including a light-reflecting inner surface and means for exposing a sample at the inner surface, said integrating sphere being disposed in the spectrophotometer so as to receive therein flashes of light emitted by said pulsatable xenon flashtube;
   a light sensor for sensing the intensity of the flashes of light as emitted by said xenon flashtube;
   said detecting means including a spectroscope for detecting the intensity of respective wavelengths of light;
   switching means disposed in an optic path defined in the spectrophotometer between said integrating sphere and said spectroscope for alternately allowing a flash of light reflected from the inner surface of the integrating sphere and a flash of light reflected from a sample exposed at said inner surface to pass along the optic path;
   an optical system disposed along the optic path for directing light reflected from the inner surface of said integrating sphere and light reflected from a sample exposed at the inner surface of said integrating sphere to said spectroscope; and
   a synchronizing sensor operatively connected to said switching means for detecting the timing in which said switching means alternately allows the flashes of light to pass along the optic path.

5. A spectrophotometer as claimed in claim 4, and further comprising compensation means operatively connected to said light sensor and said spectroscope for allowing said spectroscope, in the detections thereof, to compensate for fluctuations in the intensity of the flashes of light emitted by said xenon flashtube by calculating a ratio of the intensity of a respective flash of light reflected from the inner surface of said integrating sphere to the intensity of the respective flash of light as emitted by said xenon flashtube, and the ratio of the intensity of a respective flash of light reflected from a sample exposed at the inner surface of said integrating sphere to the intensity of the respective flash of light as emitted by said xenon flashtube while flashes of light are being emitted from said xenon flashtube.

6. A spectrophotometer as claimed in claim 4, and further comprising compensation means operatively connected to said light sensor and said spectroscope for allowing said spectroscope, in the detections thereof, to compensate for fluctuations in the intensity of the flashes of light emitted by said xenon flashtube by calculating the ratio of the sum of the intensities of the respective flashes of light reflected from a sample exposed at the inner surface of said integrating sphere to the sum of the intensities of the respective flashes of light as emitted by said xenon flashtube, and the ratio of the sum of the respective intensities of flashes of light reflected from the inner surface of said integrating sphere to the sum of the respective intensities of flashes of light as emitted by said xenon flashtube while flashes of light are being emitted from said xenon flashtube.

* * * * *